United States Patent [19]

Hillis et al.

[11] Patent Number: 4,778,267

[45] Date of Patent: Oct. 18, 1988

[54] AMBLYOPIA SCREENING

[75] Inventors: Argye I. Hillis, Waco, Tex.; Anne F. Walonker, Lomita; Kenneth R. Diddie, San Marino, both of Calif.

[73] Assignees: The Johns Hopkins University, Baltimore, Md.; University of Southern California, Los Angeles, Calif.

[21] Appl. No.: 356,141

[22] Filed: Mar. 8, 1982

[51] Int. Cl.⁴ ............................................. A61B 3/02
[52] U.S. Cl. .................................... 351/203; 351/239; 351/240; 351/244; 351/243
[58] Field of Search ............... 351/203, 239, 240, 243, 351/244, 246

[56] References Cited

U.S. PATENT DOCUMENTS

| | | |
|---|---|---|
| 1,990,218 | 2/1935 | Bailey . |
| 2,070,849 | 2/1937 | Sherman . |
| 2,089,863 | 8/1937 | UpDegrave ........................ 351/203 |
| 2,213,467 | 9/1940 | Greenspoon . |
| 2,422,384 | 6/1947 | Alexander ........................ 351/203 |
| 2,837,087 | 6/1958 | Sawyer . |
| 2,897,816 | 8/1959 | Williams . |
| 3,547,528 | 12/1970 | Weisfeld . |
| 3,842,822 | 10/1974 | Levinson et al. . |

FOREIGN PATENT DOCUMENTS

| | | | |
|---|---|---|---|
| 130628 | 4/1978 | Fed. Rep. of Germany ...... 351/203 |
| 703776 | 2/1954 | United Kingdom ................ 351/203 |

OTHER PUBLICATIONS

"Ophthalmic Instruments and Equipment" Catalog, 42 A, 1978; p. 58.
"1981 Opthalmic Instrument Catalog", West Coast Optical Instruments, Inc.; pp. 162–165.

Primary Examiner—Rodney B. Bovernick
Attorney, Agent, or Firm—Cushman, Darby & Cushman

[57] ABSTRACT

Pre-literate children are screened for amblyopia utilizing a simple device. A pair of eyepieces are mounted by a static structure so that the fields of view through the eyepieces are segregated. A card having two different, spaced pictorial representations of common physical objects or beings is mounted to the static structure so that the pictorial representations are visible through the eyepieces. If the pre-literate child is not able to accurately report both of the different pictorial representations on the card, the child is sent for more detailed testing.

14 Claims, 1 Drawing Sheet

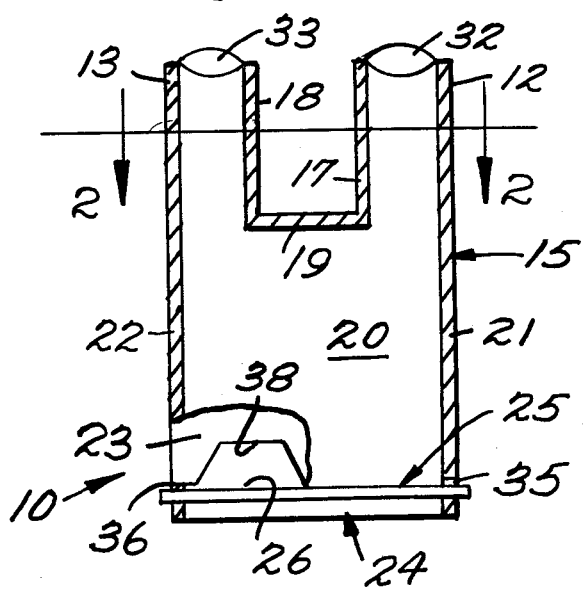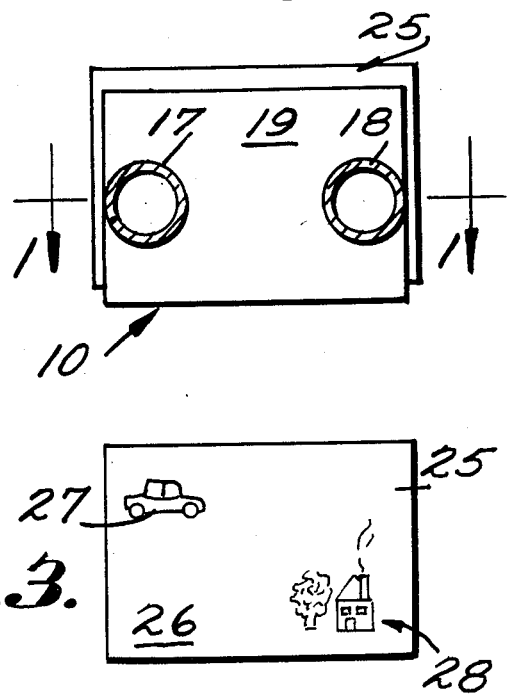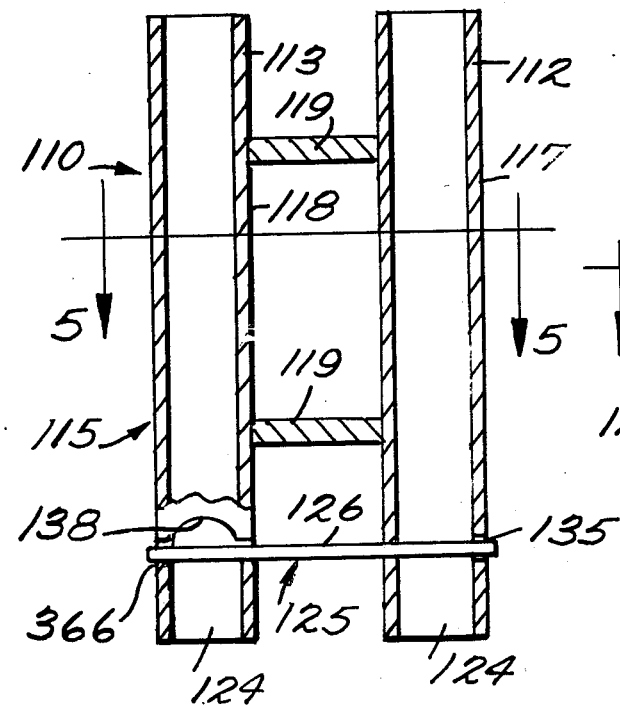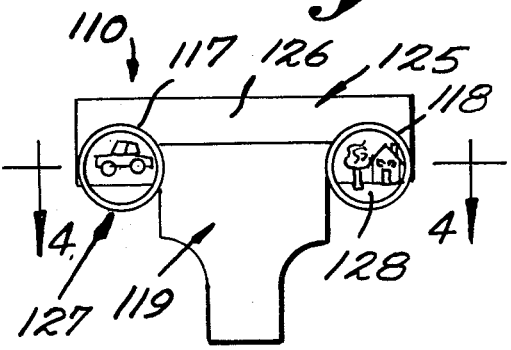

AMBLYOPIA SCREENING

BACKGROUND AND SUMMARY OF THE INVENTION

Amblyopia is a dimness of vision in the absence of a demonstrable structural defect, and it may occur gradually or suddenly and may effect both eyes or one eye. Amblyopia is often difficult to diagnose, and especially so in pre-literate children. Since proper treatment of amblyopia can be dependent upon how early it can be detected, it is desirable to recognize amblyopia in pre-literate children as early as possible. In this way learning problems associated with the dimness of vision, particularly dimness of central vision, for pre-literate children can be overcome.

The invention relates to a method for screening pre-literate children for amblyopia and a simple screening device for use in accomplishing that purpose. The invention only relates to screening, and is not intended to provide positive diagnosis of amblyopia. However after screening according to the invention is practiced, those children without an amblyopic condition can be clearly identified, and any children falling outside of that category can be sent for more detailed testing. In this way unnecessary detailed testing of a large number of children is avoided, yet positive diagnosis of those having an amblyopic condition is facilitated.

The simple screening device according to the invention comprises no moving parts although an indicia-containing card forming part of the structure may be removable and replaceable if desired. A pair of eyepieces are mounted by a static structure which segregates the fields of view through the eyepieces and maintains a fixed static relationship between them. The indicia-containing card has a face thereof with two different, spaced indicia formed thereon, the indicia each being a pictorial representation of a common physical object or being, so that a preliterate child will have no difficulty in identifying the object. The card is either permanently or detachably mounted to the static structure so that each pictorial representation is visible through one of the eyepieces, but not the other.

The method of screening pre-literate children for amblyopia according to the present invention utilizes the simple screening device so that the card is placed in association with the eyepieces with one pictorial representation in the field of view through each eyepiece. The pre-literate child then looks into the eyepieces, one eye associated with each eyepiece, and reports what pictorial representations he or she sees. The report can be verbal, or the reporting sequence can be non-verbal if desired. In a nonverbal report the child would be asked merely to select from a number of pictures or tiles any objects he or she sees by looking into the eyepieces. For any child that does not accurately report both of the different pictorial representations contained on the card, more detailed testing is provided.

The present invention provides an extremely simple yet effective way for screening pre-literate children for amblyopia. No complicated apparatus or expensive equipment is provided. The invention merely employs a few static components, utilizes ambient light, and amblyopia screening utilizing the invention may be practiced in a matter of seconds for each child.

It is the primary object of the present invention to provide a simple, yet effective, method and apparatus for screening pre-literate children for amblyopia. This and other objects of the present invention will become clear from an inspection of the detailed description of the invention, and from the appended claims.

BRIEF DESCRIPTION OF THE DRAWINGS

FIG. 1 is a top view, partly in cross-section and partly in plan, of an exemplary amblyopia screening device according to the present invention, the cross-section along lines 1—1 of FIG. 2;

FIG. 2 is an end cross-sectional view of the device of FIG. 1, taken along lines 2—2 thereof;

FIG. 3 is an end view of a typical indicia card forming a part of the apparatus of FIGS. 1 and 2;

FIG. 4 is a top cross-sectional view, with the indicia-containing card shown in plan, of another embodiment of the screening device according to the present invention, the cross-section taken along lines 4—4 of FIG. 5; and FIG. 5 is an end cross-sectional view of the embodiment of FIG. 4 taken along lines 5—5 thereof.

DETAILED DESCRIPTION OF THE DRAWINGS

A first embodiment of an exemplary amblyopia screening device according to the invention is shown by reference numeral 10 in FIGS. 1 and 2, and a second embodiment is shown generally by reference numeral 110 in FIGS. 4 and 5. Structures of the embodiment of FIGS. 4 and 5 corresponding to structures in the FIGS. 1 and 2 embodiment have the same reference numeral, only preceded by a "1".

The basic components of the device 10 comprise a pair of eyepieces 12, 13, the eyepiece 12 for the left eye and the eyepiece 13 for the right eye. A static structure, shown generally by reference number 15, comprises means for segregating the fields of view of the eyepieces 12, 13 and maintains them in a fixed static relationship with respect to each, i.e., spaced apart the normal width between a preliterate child's eyes. In the embodiment of FIGS. 1 and 2, the static structure 15 comprises a pair of short tubular extensions 17, 18 of the eyepieces 12, 13, respectively, which connect to a hollow box through a side wall 19 thereof. The box also has a solid bottom 20 (see FIG. 1), a pair of opposite solid side walls 21, 22, and may have a top 23 (see FIG. 1). Preferably the wall opposite the wall 19 is open, as illustrated by reference numeral 24 in FIG. 1, although it may be closed if desired.

A further important component of the device 10 comprises an indicia-containing card 25. The card 25 has a face 26 thereof on which two different, spaced indicia are formed. The indicia 27, 28 each comprises a pictorial representation of a common physical object or being, such as a car, house, tree, dog, or the like. The object being represented should be one that the vast majority (if not all) of pre-literate children to be screened would be very familiar with. For the embodiment of FIGS. 1 and 2, the eyepieces 12, 13 include lenses 32, 33 through which the card 25 is viewed, and the pictorial representations 27, 28 are spaced from each other in two dimensions (e.g., horizontally and vertically).

The device 10 also comprises means for mounting the card 25 to the segregating and maintaining means 15 so that each pictorial representation 27, 28 on the card 25 is visible to the child using the device 10 through one of the eyepieces 12, 13, but not the other. For instance, the mounting means may comprise means defining a slit 35 in side wall 21, and a slit 36 in side wall 22, each of the slits being spaced the same distance from the eyepieces 12, 13, and being open at the top of the means 15 so that the card 25 may be slid into the slits 35, 36 with a downward force and be removed therefrom with an upward force. The slits 35, 36 hold the card steady.

If desired, the card 25 could be fixed to the walls 21, 22 and/or bottom 20, however it is desirable to provide interchangeability of cards 25 so that if the children to be screened are all in the same general area prior to testing they cannot provide correct answers merely by listening to the children before them, the card 25 being changed for each child.

In order to ensure that the indicia 27, 28 are visible during viewing, one or more cutouts 38 may be formed in the top 23 of the device 10 to let in ambient light right at the card 25. Alternatively, or in addition, the card 25 may be transluscent (e.g., light cardboard or plastic), with ambient light entering through the open end 24 providing sufficient illumination of the indicia 27, 28.

In the embodiment illustrated in FIGS. 4 and 5, the segregating and maintaining means 115 takes a different form. Long (e.g., 13-inch) tubular extensions 117, 118 are associated with the eyepieces 112, 113, and the eyepieces preferably do not include lenses. At least one cross-member 119 is provided connecting the extensions 117, 118 together so that there is a fixed predetermined spacing therebetween. One or all of the cross-members 119 may be formed with a bottom portion 40 (see FIG. 5) which may serve as a handle for holding the device 110, or a supporting leg for placing it on a table, for receipt within a holding bracket, or the like.

The card 125 in the FIGS. 4 and 5 embodiment has the pictorial representations 127, 128, formed thereon spaced in only one dimension (e.g., horizontally) the same distance apart as the eyepieces 112, 113. The solely horizontal spacing may be more effective for amblyopic children with a central suppression. The card 125 may be removably mounted in slits 135, 136 formed in the tubular extensions 117, 118, respectively, and light for viewing the indicia 127, 128 may be provided by cutouts 138 and/or by open ends 124 of the extensions 117, 118.

A method of screening pre-literate children for amblyopia utilizing a device 110 is as follows:

A card 125 with distinct pictorial representations 127, 128 is placed in slots 135, 136, with the face 126 facing the eyepieces 112, 113. A pre-literate child is then asked to look into the eyepieces 112, 113, one eye associated with each eyepiece, and report what pictorial representation he or she sees. The report provided by the child can be verbal, or if desired or necessary non-verbal. A nonverbal would be provided by having a number of pictures or tiles in the screening area, some of which had pictures identical to the representations 127, 128. The child could merely then select from the group of pictures or tiles the ones corresponding to those he or she saw in the device 110. If the child accurately reports both of the pictorial representations 127, 128, there is little likelihood the child has amblyopia. However, if the child inaccurately reports one or both of the representations, or does not see one or both of the representations, the child is scheduled for further more detailed testing.

It will thus be seen that according to the present invention a simple and effective method-and apparatus for screening pre-literate children for amblyopia have been provided.

While the invention has been herein shown and described in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent structures and methods.

What is claimed is:

1. A method for screening pre-literate children for amblyopia, utilizing a screening device having a pair of eyepieces, means for segregating the fields of view through the eyepieces, and an indicia-containing card mounted in the fields of view through the eyepieces, the card having two different separate indicia formed thereon, one indicia in each field of view, and the indicia each being a pictorial representation of a common physical object or being, said method comprising the steps of:

placing the card in association with the eyepieces so that one pictorial representation is in the field of view through each eyepiece, and cannot be seen through the other;

having a pre-literate child look into the eyepieces, one eye associated with each eyepiece, and report what pictorial representations he or she sees; and providing further more detailed testing for the child if the child does not accurately report both of the different pictorial representations contained on the card.

2. An amblyopia screening device consisting of:

a pair of eyepieces;

a static structure, devoid of moving parts, comprising means for segregating the fields of view through the eyepieces; and maintaining the eyepieces in a fixed static relationship with repsect to each other;

an indicia containing card having a face thereof with two different, spaced, indicia formed thereon, the indicia each being a pictorial representation of a common three-dimensional physical object or being, the incidia not meshing when viewed binocularly; and means for mounting said card to said segregating and maintaining means so that each pictorial representation on said card is visible through one of said eyepieces, but not the other, and so that said card is fixed with respect to said eyepieces, said static structure including a pair of tubular continuations of said eyepieces and at least one cross-member connecting said tubular continuations together the means for mounting said card being positioned along said tubular continuations.

3. A device as recited in claim 2 wherein each of said eyepieces has a lens mounted therein.

4. A device as recited in claim 3 wherein said pictorial representations on said card are displaced from each other in two dimensions.

5. A device as recited in claim 2 wherein said card is transluscent and wherein said means for mounting said card so that the pictorial representations thereon are visible comprises means for supplying ambient light to said card on the opposite side thereof as said eyepieces and as said indicia-containing face thereof.

6. A device as recited in claim 2 wherein said means for mounting said card so that the pictorial representations thereon are visible comprises means for supplying ambient light to said card face containing said indicia.

7. A device as recited in claim 2 wherein said static structure consists of: a pair of tubular extensions of said eyepieces; and a hollow box having at least three solid side walls and a solid bottom wall, the tubular extensions connected to a first solid side wall of the box and in communication with the hollow interior thereof; and wherein said means for mounting said card to said segregating and maintaining means comprises a slit formed in each of two oppposite side walls distinct from said first solid side wall, said slit having a width sufficient to receive said card therein and hold it steady.

8. An amblyopia screening device consisting of:
a pair of eyepieces;
a pair of static tubular continuations of said eyepieces;
at least one static cross-member rigidly connecting said tubular continuations together to maintain them a predetermined fixed distance apart;
an indicia containing card having a face thereof with two different, spaced, indicia formed thereon, the indicia being spaced substantially the same distance as the spacing of said eyepieces, and the indicia each being a pictorial representation of a common physical object or being; and
means defining a slit in each of each eyepiece tubular continuations at the same fixed distance remote from the eyepiece with which said tubular extension is associated, and having a width sufficient to recieve said card therein and hold it steady.

9. A device as recited in claim 8 wherein each of said eyepieces has a lens mounted thereon.

10. A device as recited in claim 9 wherein said pictorial representations on said card are displaced from each other in one dimension only.

11. A device as recited in claim 7 wherein said pictorial representations on said card are displaced from each other in two dimensions.

12. A device as recited in claim 2 wherein said pictorial representations on said card are displaced from each other in two dimensions.

13. An amblyopia screening device consisting of:
a pair of eyepieces;
a static structure, devoid of moving parts, comprising means for segregating the fields of view through the eyepieces; and maintaining the eyepieces in a fixed static relationship with respect to each other;
an indicia containing card having a face thereof with two different, spaced, indicia formed thereon, the indicia each being a pictorial representaion of a common three-dimensional physical object or being, the indicia not meshing when viewed binocularly; and
means for mounting said card to said segregating and maintaining means so that each pictorial representation on said card is visible through one of said eyepieces, but not the other, and so that said card is fixed with respect to said eyepieces,
wherein said pictorial representaions are displaced from each other in one dimension only, and said static structure consists of: a pair of tubular continuations of said eyepieces; and at least one cross-member rigidly connecting said tubular continuations together; and
wherein said means for mounting said card to said segregating and maintaining means comprises a slit formed in each of said tubular continuations at the same fixed distance remote from the eyepiece with which said tubular extension is associated, and having a width sufficient to receive said card therein and hold it steady.

14. An amblyopia screening device consisting of:
a pair of eyepieces;
a static structure, devoid of moving parts, comprising means for segregating the fields of view through the eyepieces; and maintaining the eyepieces in a fixed static relationship with repsect to each other;
an indicia containing card having a face thereof with two different, spaced, indicia formed thereon, the indicia each being a pictorial representation of a common three-dimensional physical object or being, the indicia not meshing when viewed binocularly; and
means for mounting said card to said segregating and maintaining means so that each pictorial representation on said card is visible through one of said eyepieces, but not the other, and so that said card is fixed with respect to said eyepieces,
wherein said static structure consists of: a pair of tubular extensions of said eyepieces; a hollow box having at least three solid sidewalls and a solid bottom wall, the tubular extensions connected to a first solid sidewall of the box and in communication with the hollow interior thereof; and
wherein said means for mounting said card to said segregating and maintaining means comprises a slit formed in each of two opposite sidewalls distinct from said first solid sidewall, said slit having a width sufficient to receive said card therein and hold it steady.

* * * * *